(12) United States Patent
Thompson

(10) Patent No.: US 11,738,176 B2
(45) Date of Patent: Aug. 29, 2023

(54) ORGANIZING, ANCHORING, SAFETY DEVICE FOR PERIPHERAL INTRAVENOUS CATHETERS

(71) Applicant: Avant-Garde Healthcare Solutions, Inc., Glen Burnie, MD (US)

(72) Inventor: Lynita Thompson, Glen Burnie, MD (US)

( * ) Notice: Subject to any disclaimer, the term of this patent is extended or adjusted under 35 U.S.C. 154(b) by 160 days.

(21) Appl. No.: 17/146,104

(22) Filed: Jan. 11, 2021

(65) Prior Publication Data

US 2021/0213254 A1 Jul. 15, 2021

Related U.S. Application Data

(60) Provisional application No. 62/959,253, filed on Jan. 10, 2020.

(51) Int. Cl.
A61M 25/02 (2006.01)

(52) U.S. Cl.
CPC ....... *A61M 25/02* (2013.01); *A61M 2025/024* (2013.01); *A61M 2205/584* (2013.01); *A61M 2209/088* (2013.01)

(58) Field of Classification Search
CPC ............ A61M 25/02; A61M 2025/024; A61M 2205/584; A61M 2209/088; A61M 2025/0246; A61M 2025/0266; A61M 2025/028; A61M 2025/0206; A61M 2025/0213; A61M 2025/0253; A61M 2025/026; A61M 16/0497; A61M 16/0488
See application file for complete search history.

(56) References Cited

U.S. PATENT DOCUMENTS

| | | | |
|---|---|---|---|
| 5,916,199 A | * | 6/1999 | Miles .................. A61M 25/02 604/174 |
| 7,967,792 B2 | | 6/2011 | Bierman |
| 8,500,698 B2 | | 8/2013 | Kyvik et al. |
| 8,556,859 B2 | | 10/2013 | Nilson et al. |
| 8,834,427 B2 | | 9/2014 | Kyvik et al. |
| 8,979,805 B1 | | 3/2015 | Khalaj |
| 9,017,290 B2 | | 4/2015 | Peters et al. |
| 10,350,388 B2 | | 7/2019 | Kyvik et al. |
| 2010/0114034 A1 | * | 5/2010 | Wright ................. A61M 25/02 604/177 |
| 2012/0216385 A1 | * | 8/2012 | Taylor .................. A61M 25/02 428/156 |
| 2012/0271240 A1 | * | 10/2012 | Andino ................ A61M 25/02 604/180 |
| 2014/0228810 A1 | * | 8/2014 | Rosenberg ........... A61M 25/02 604/513 |

\* cited by examiner

*Primary Examiner* — Bhisma Mehta
*Assistant Examiner* — Phoebe Anne Staton
(74) *Attorney, Agent, or Firm* — Larry J. Guffey, Esq.; Oliver & Grimsley, LLC

(57) ABSTRACT

An organizing, safety and securement device for use with a peripheral intravenous catheter includes: (a) a catheter base with an opening, that is covered by a transparent membrane, and an upper securement element with a luer fitting indentation, (b) a lower securement element having a top surface with a luer fitting indentation (c) an organizer base with upper and lower clamping members that are hinged together and have free surfaces with tubing indentations that include color coded, mainline and apinch tubing portions, and (d) a tether which connects the catheter and organizer bases.

10 Claims, 5 Drawing Sheets

ORGANIZING, ANCHORING, SAFETY DEVICE FOR PERIPHERAL INTRAVENOUS CATHETERS

CROSS-REFERENCE TO RELATED APPLICATION

This application claims the benefit of Provisional Patent Application No. 62/959,253, filed Jan. 10, 2020 by the present inventor. The teachings of this earlier application are incorporated herein by reference to the extent that they do not conflict with the teaching herein.

BACKGROUND OF THE INVENTION

1. Field of the Invention

The present invention generally relates to surgery and means for securing conduits to a body. Specifically, the invention is directed to an organizing, safety and securement means or device and its related methods for dealing with peripheral intravenous catheters.

2. Description of the Related Art

Medical treatment of patients frequently involves the use of peripheral intravenous catheters to direct fluids into the bloodstream. The fluid (e.g., parenteral liquid, blood, medication or anesthesia) typically drains from a container positioned above the patient. The fluid flows through tubing and into the catheter. The catheter and fluid tubing are commonly removably attached by a luer-type or luer connector, adapter or fitting.

In common practice, a health care provider uses adhesive or surgical tape to maintain the catheter in place on the skin of the patient. The connection between the tubing and the catheter is likewise maintained by use of tape. A safety loop may also be formed in the tubing so that any tension applied to the tubing is absorbed by the slack of the safety loop and does not directly pass to the catheter, and typically this loop is also taped to the skin of the patient.

Furthermore, this catheterization process can often requires frequent disconnections between the catheter and the fluid supply tube (e.g., to replace the tubing on a frequent basis, to inspect the insertion point for inflammation or infection, to change a patient's dressing gown) which can necessitate a repeat of the above-described taping procedures. This frequent application and removal of surgical tape can result in the excoriation of the skin of the patient in the area of the insertion.

Also, it can happen that the integrity of the catheter's fluid flow is interrupted when there are problems with the adhesive tape's ability to secure the catheter to the patient's skin due to, for example, accidental tugging or pulling on the tubing that is attached to the catheter. This situation often happens during times when the patient is anxious, combative or has suffered a considerable amount of blood loss due to their medical status. These can be high acuity instances when the patient needs to have a stabilized intravenous access for the administration of life saving medications, intravenous fluids or a blood transfusion. Avoiding such interruptions and keeping the time required to reestablish the intravenous feed to a minimum can be critical.

Additional safety concerns can arise when the patient needs to be simultaneously, intravenously receiving multiple types of fluids, some of which can be mixed (plain intravenous fluids or medications that can be mixed without adverse effects) and other that cannot (e.g., anti-infectives, patient controlled analgesia, potassium/electrolytes, insulin drips, narcotics, chemotherapy, heparin/anti-coagulants). Avoiding fluid-mixing mistakes in these situations can be a life or death matter.

A number of catheterization systems have been developed to address many of the above listed concerns (i.e., securement, minimize stress on the patient's skin, safety concerns related to fluid mixing mistakes). See, for example, U.S. Pat. Nos. 10,350,388; 9,017,290; 8,979,805; 8,834,427; 8,556,859; 8,500,698 and 7,967,792.

In spite of these advancements, there still continue to be widespread reports of problems and dissatisfaction with current peripheral, intravenous catherization systems or devices. Thus, there continues to exist a need to improve the methods and devices that are used in current peripheral, intravenous catherization procedures.

DESCRIPTION OF THE PREFERRED EMBODIMENT

Figure 1:
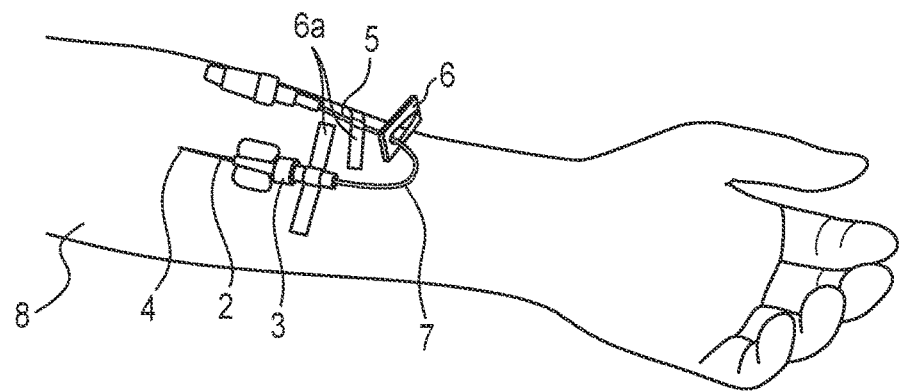
FIG. 1 shows an illustration of the prior art practice of using considerable amounts of surgical tape to secure a peripheral, intravenous catheter on a patient's arm.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention generally relates to improved methods and means for peripheral, intravenous catherization systems or devices, including those that provide for the enhanced securement of the device, minimizing the adverse consequences of the use of the device on a patient's skin, and providing the means for better organizing multiple intravenous lines so as to avoid fluid mixing mistakes.

FIG. 1 shows the typical, prior art practice of using considerable amounts of surgical tape to maintain or secure a peripheral, intravenous catheter 2 in place on the skin of the arm 8 of a patient. In this instance, the catheter has the typical luer fitting 3 upstream of the catheter's cannula 4. This catherization assembly also has a short length of tubing 5 with the appropriate luer connectors at both ends and a clamping means 6 attached to the tubing to help regulate the flow rate of the fluid through the tubing. It can also be considered to have something of a safety loop 7 in the tubing so that any tension applied to the tubing is absorbed by the slack of the safety loop and does not directly pass to the catheter.

It should also be noted that the catherization assembly shown is a relatively simple one compared to other, more complex assemblies that may have additional features (e.g., a Y-connector immediately upstream of the catheter's luer fitting so as to allow for two tubing lines that lead to their own fluid containers/reservoir, each of which has a different fluid; thereby allowing these differing fluids to pass through the same opening in the patient's arm, an injection port connector for the insertion of a syringe that can be used to, on a-one-time basis, insert medication through the catheter and into the patient's vein). These additional features can also require additional surgical tape 6a or taping on other parts of the patient's arm.

Figure 2:
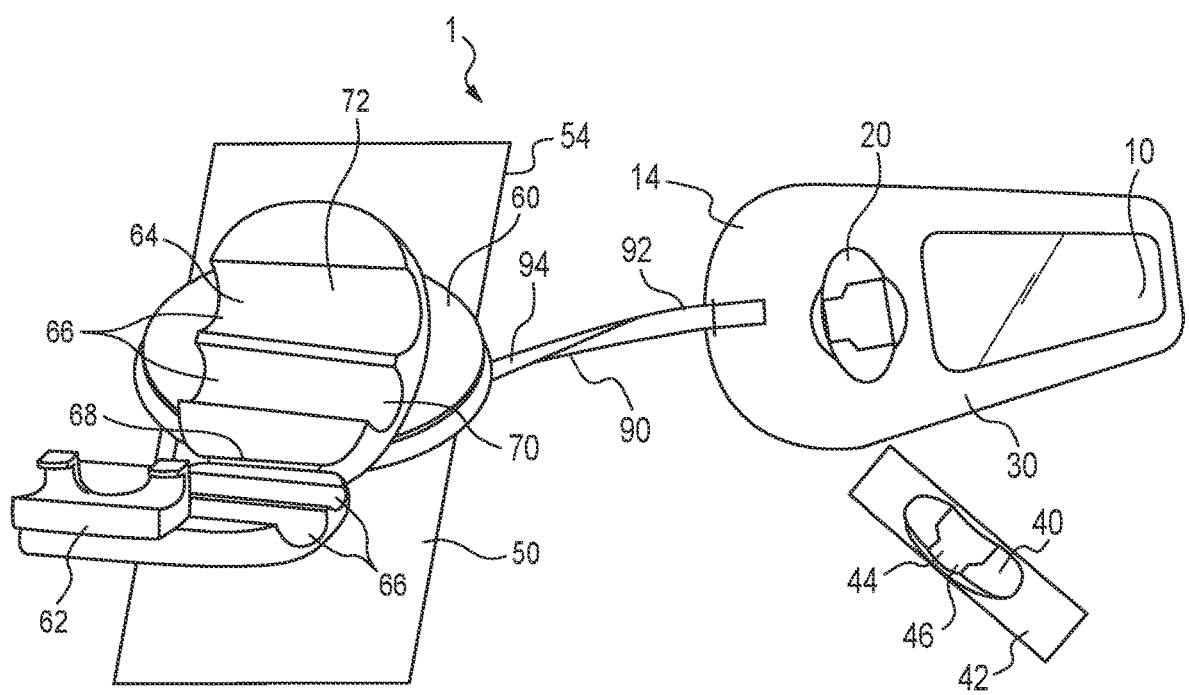
FIG. 2 shows an illustration of a perspective view of a preferred embodiment of the present invention.

Shown in FIG. 2 is a perspective view of a preferred embodiment of the present invention. It is an organizing, anchoring (securement) and safety device or sysytem 1, or PIVOASS, for use with a wide variety of peripheral intravenous (PIV) catheter assemblies. Its major components are a peripheral intravenous catheter base or catheter base 10, a tubing organizer base or organizer base 50 and a tether 90 that has a downstream end 92 to which the catheter base is attached and an upstream end 94 to which the organizer base is attached. The tether shown in FIG. 2 has been rotated 180 degrees in passing from its upstream to its downstream; this allow the top surface 52 of the organizer base and the bottom surface 14 of the catheter base to be shown in this single perspective view.

The top surface 52 of the organizer base 50 is shown because it has an attached organizer 60 that has two color-coded passageways. One 70 of which is used by mainline tubing 5a through which can flow only fluids that can be mixed, while the other passageway 72 is used by apinch tubing through which can flow only fluids that cannot be mixed (e.g., high risk medicines such as anti-infective agents, anti-psychotics, potassium, insulin, narcotics and sedative agents, chemotherapy and heparin and other anti-coagulants—these are represented in the medical community by the acronym 'A PINCH' or apinch).

The bottom surface 14 of the catheter base 10 is shown because it has attached to it a securement element or means 20 that is configured to interact with top, outer surface of the catheter's luer fitting 3 so as to help prevent the catheter's movement once the tip of its cannula 4 has been inserted into the vein of a patient. Interacting, for this same purpose, with the with bottom, outer surface of the catheter's luer fitting 3 is a cradle assembly or means 40 which is itself attached to the top surface of a cradle base 42 whose bottom surface has an adhesive that is used to releasably attach the cradle base to a patient's skin.

Figure 3A:
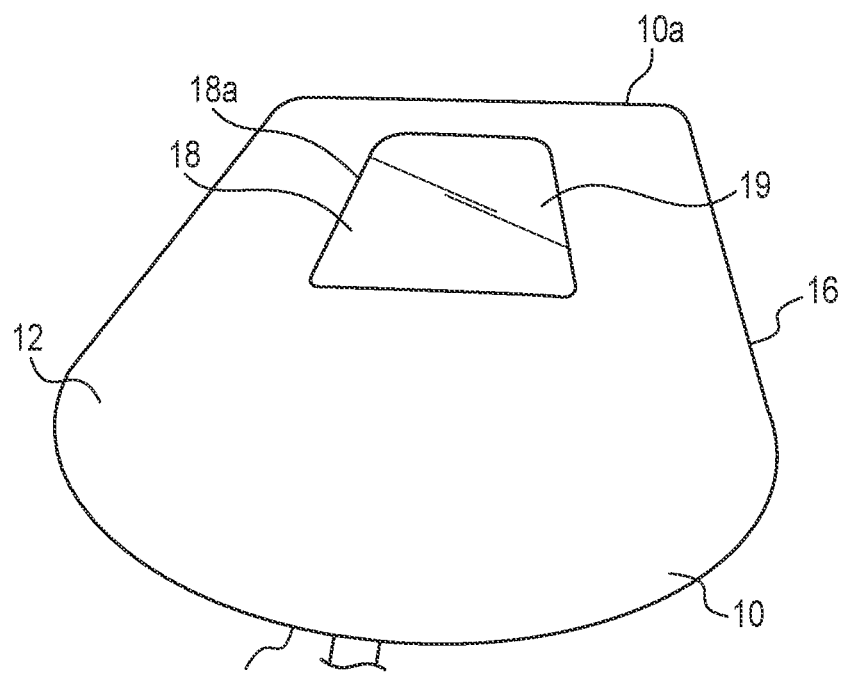
FIG. 3A shows an illustration of a perspective, top surface view of a preferred embodiment of the catheter base of the present invention.
Figure 3B:
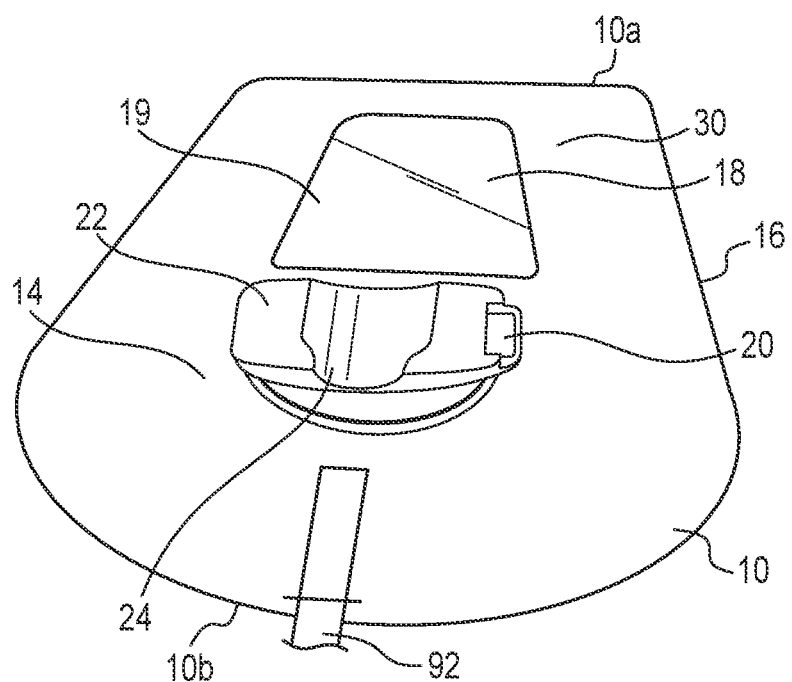
FIG. 3B shows an illustration of a perspective, bottom surface view of a preferred embodiment of the catheter base of the present invention.

FIGS. 3A and 3B show, respectively, the top 12 and bottom 14 surfaces of the catheter base 10. It has an elongated shape and extends between its downstream 10a and upstream 10b ends. This base has a boundary edge 16 and is made from a thin foam material. Proximate its downstream edge is a first portion that includes an opening 18, which has a perimeter 18a that extends between its top and bottom surfaces. A transparent membrane 19 covers this opening by having its edges adhered to this base's bottom surface.

When the PIVOASS is in use, this opening 18 will be placed over the insertion point where the catheter's cannula 4 enters a patient's skin so as to allow a caregiver to visually monitor this insertion point to help ensure that the patient's skin in this area is not adversely impacted by the use of the catheter. A medical grade adhesive 30 is used on this base's bottom surface 14 and around the edges of the transparent membrane to attach the catheter base to a patient's skin and seal the area around the catheter's insertion point from infection-causing micro-organisms, etc. entering the area.

The securement element or means 20 which is attached to a second portion of the catheter's base's bottom surface 14 is seen to be configured so that it can interact with top of the catheter's luer fitting 3 to help prevent the catheter's movement once the tip of its cannula 4 has been inserted into the vein of a patient and the catheter base's adhesive is being used to secure the base to the patient's skin. See FIG. 3C which shows an illustration of the peripheral intravenous catheter's base and its upper securement element or securement means 20 hovering over the top surface of a catheter's luer fitting and when its bottom surface is about to be placed in the lower securement element or cradle means 40 which is attached to the top surface of the cradle base 42 that has been attached to a patient's skin. Both the securement 20 and cradle 40 means will typically be plastic elements with outer or free surfaces 22 (upper-securement-element free surface), 44 (lower-securement-element free surface), that contain indentations 24, 46 or unique shapes that have been designed to interact with the configuration of the luer fitting's outer surface so as to securely lock it in place once these elements are properly aligned and adhered to the luer fitting and the catheter 10 and cradle 42 bases have been secured to a patient's skin.

Figure 3C:
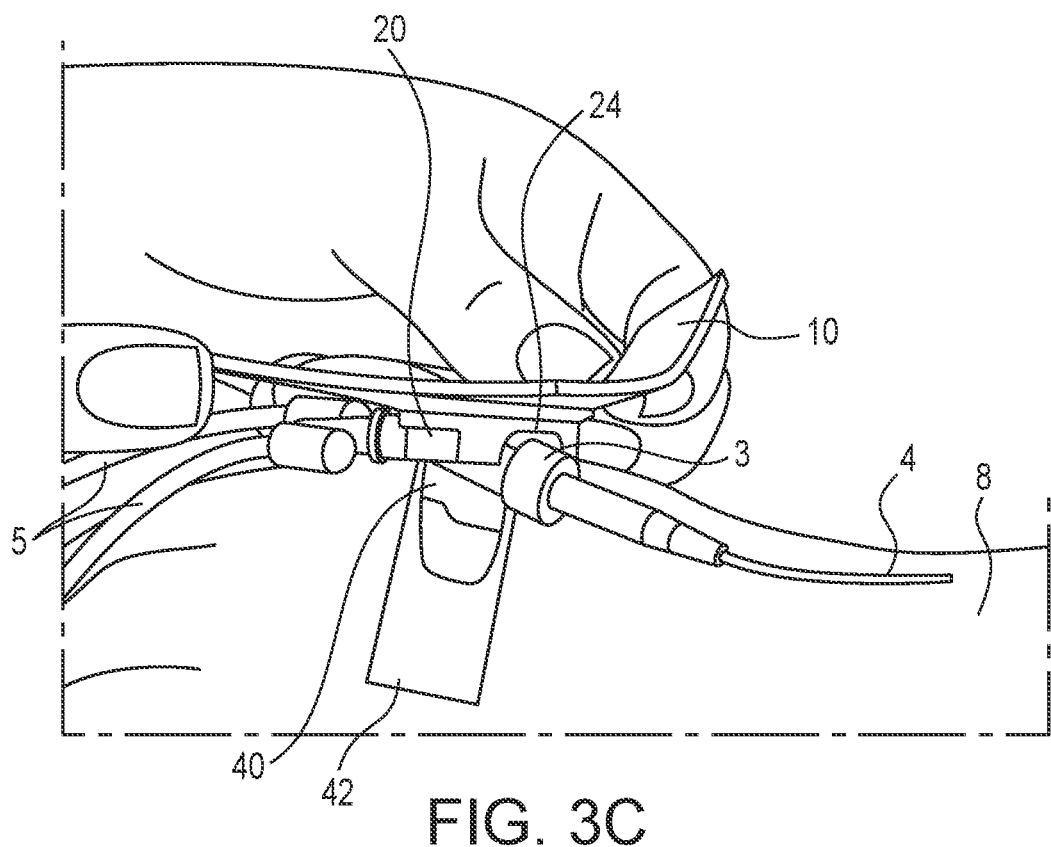
FIG. 3C shows an illustration of a perspective view of the present invention's catheter base and its securement means hovering over the top surface of a catheter's luer fitting and when its bottom surface is about to be placed in the present invention's cradle means which is attached to the top surface of its cradle base that has been releasably attached to a patient's skin.

Note also in FIG. 3C that two tubing lines appear to be connected to the catheter shown. This suggests that a Y-connector is being used just upstream of the luer fitting so as enable these two pieces of tubing to connect through the Y-connector to the catheter. This is often a preferred mode of operation as it allows a second fluid or medicine to flow into the patient's vein through the single injection point.

A significant advantage of the present invention over the prior art, where only tape is being used to anchor a catheter and its intravenous tubing, is that the catheter and cradle bases provide significant, additionally anchoring ability for the catheter beyond that which is provided by the adhesive which is used to adhere the portion of the catheter base surrounding its opening to a patient's skin. Additionally, the present invention 1 provides still more securement features, while also enhancing the safety in using a peripheral, intravenous catheter 2, by utilizing upstream of the catheter base a second base or an organizer base 50. See FIGS. 4A and 4B.

Figure 4A:
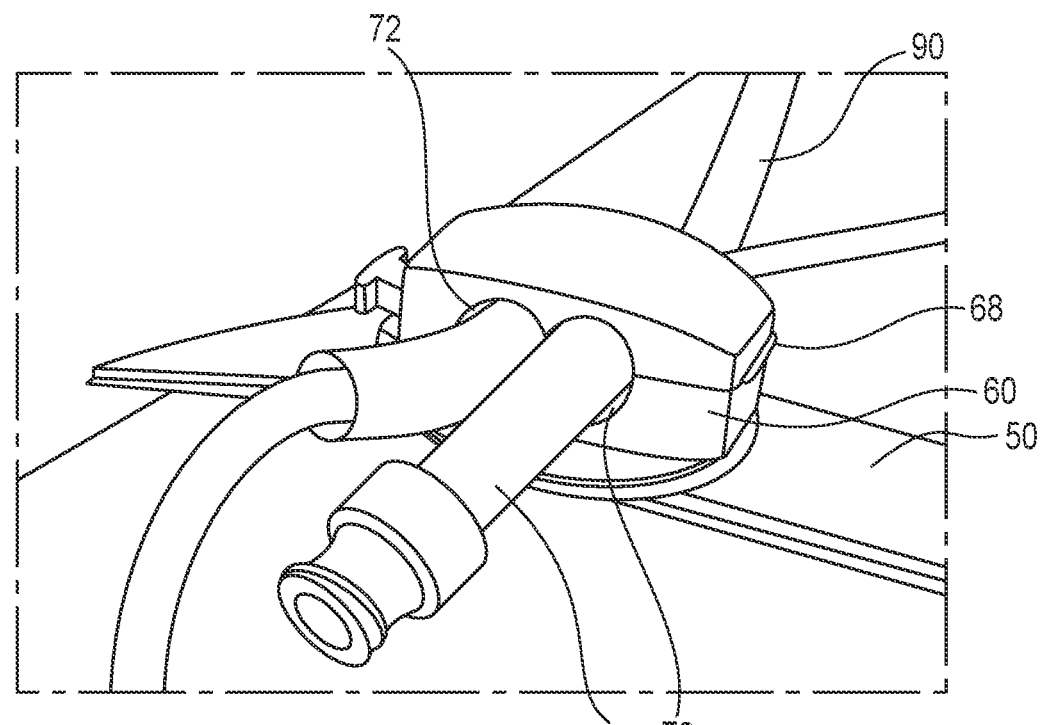
FIG. 4A shows an illustration of an upstream, perspective view of the present invention's organizer base and its attached organizer being used with mainline tubing which is passing though the organizer's color-coded (e.g., green), mainline tubing passageway.

FIG. 4A shows an upstream, perspective view of an organizer base 50 and its attached organizer 60 that is being used in this illustration with mainline tubing 5a which is passing though the organizer's color-coded (e.g., green), mainline tubing passageway 70. Meanwhile, the organizer's color-coded (e.g., red), apinch tubing passageway 72 is not in use. It should be noted that the color-coding of these passageways provides an additional, much-needed safety step in the process of initiating a new IV line as it forces the caregiver who is installing the line to take a moment and give some consideration to the type of fluid that will be used in the line and whether or not it is a high risk, apinch fluid that cannot be mixed with other fluids. To further avoid the possibility of improperly mixing medications or fluids, it is recommended that color-coded labels be applied to the tubing itself at a position on the tubing that is just upstream of where the tubing will pass through the present invention's organizer. The same type of color-coded labels are also recommended for any medication ports in the tubing.

Figure 4B:
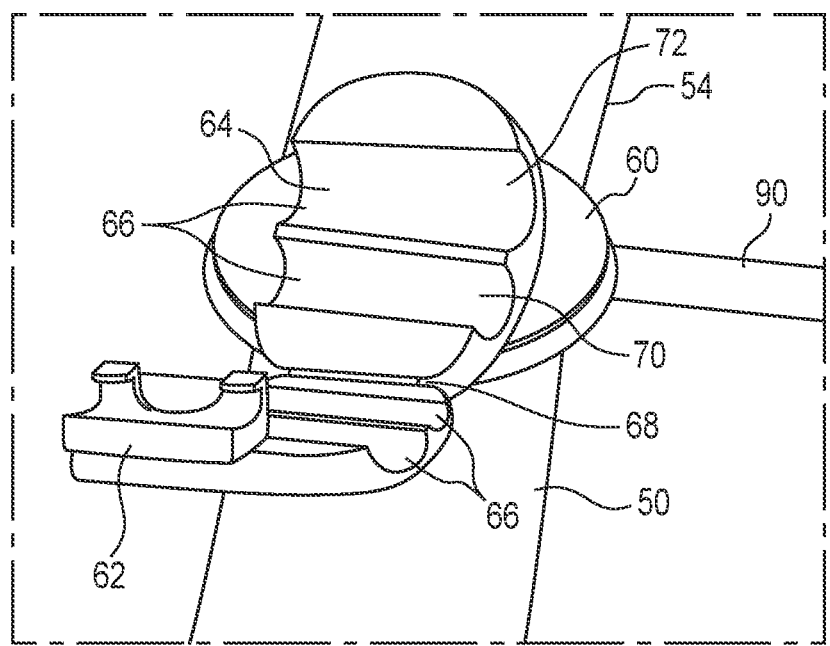
FIG. 4B shows an illustration of an elevated, perspective view of a preferred embodiment of the present invention's organizer in its "open" position.

FIG. 4B shows an elevated, perspective view of a preferred embodiment of an organizer 60 its "open" position and thus reveals that it has upper 62 and lower 64 clamping members which are hinged together on the side by a hinge 68 so as to allow the organizer's upper member to be moved upwards to temporarily gain access to either of the organizer's passageways. Indentations 66 (i.e., bottom-portion-tubing indentations that include mainline and apinch portions) in the lower member top surface and similar indentations (i.e., top-portion-tubing indentations that include mainline and apinch portions) in the upper member's bottom surface provide for the simultaneous use of both mainline and apinch tubing. These mainline and apinch portions are color coded to prevent connecting the wrong fluids to the tubing that runs through these color coded passageways. In addition to the embodiment shown, an alternative embodiment involves providing each color-coded passageway with its own individual hinged, upper and lower members that can be open and closed to accept or receive the appropriate tubing.

The organizer base's bottom surface 54 is typically coated with a medical grade adhesive to attach the organizer base to a patient's skin. The organizer base has multiple functions: (1) to secure the tubing and prevent it from dangling or tugging at the catheter's insertion site, (2) to organize medication ports for easy accessibility, (3) to signal a healthcare provider as to whether or not medications should be mixed, and (4) to prevent repetitive removal of adhesive tape from a patient's arm when changing hospital gowns or replacing tubing.

This last function is achieved by simply opening its clamping members 62, 64, while the organizer base remains attached to the patient, to remove and replace the tubing, and then reclosing the clamping members. Without this organizer base, adhesive tape would typically be used for this function and thereby result in multiple cycles of removing and replacing adhesive tape which can result in impaired skin integrity and possibly put the patient at the risk of hospital acquired infections.

Figure 5:
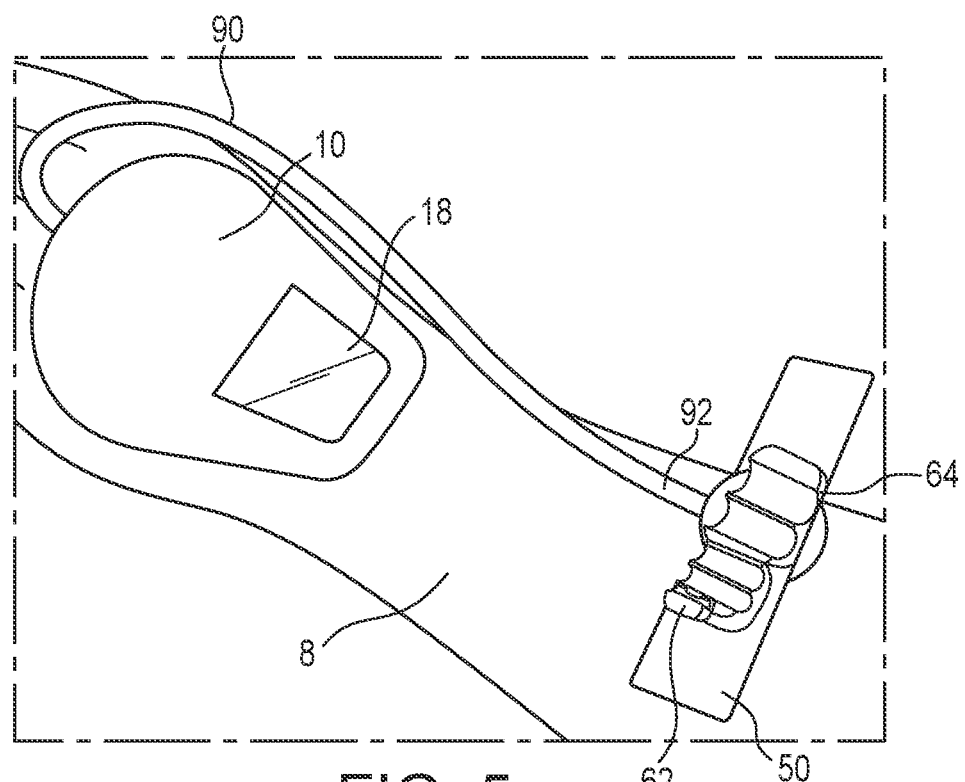
FIG. 5 shows an illustration of the general layout of the present invention as it is being positioned on a patient's arm when it is to be used with a peripheral, intravenous catheter whose cannula end is to be inserted into a vein that is approached through the skin on the top portion of a patient's hand or forearm.

FIG. 5 shows the general layout of the present invention as it is being positioned on a patient's arm when it is to be used with a peripheral, intravenous catheter 2 whose cannula end is to be inserted into a vein that is approached from the fingers and toward the wrist and through the skin on the top portion of a patient's hand. Alternatively, the peripheral, intravenous catheter's cannula end can be inserted into a patient's forearm. Unseen are the cradle means and its base that are positioned on the top portion of a patient's hand and beneath the catheter base.

Once the catheter's cannula end has been inserted, the cradle base is positioned below the catheter's luer fitting so that the cradle means can be placed against the luer fitting bottom surface so as assist in preventing any upstream or downstream motion of it. The catheter base's securement means 20 is then placed against the luer fitting's top surface above the cradle means 40 and a check is made to ensure that the catheter base's opening 18 is situated so the cannula's insertion point can be clearly seen through this opening. Once these conditions are met, the adhesive 30 on the catheter's bottom surface is used to secure the catheter base to, in this instance, the top portion of a patient's hand.

After the catheter base has been adhered to the patient's hand, the tether is rotated 180 degrees so as to locate the organizer base 50 above the catheter base and, in this instance, on the patient's forearm. Next, the tubing coming from the catheter is placed in the organizer's appropriate passageway, either mainline or apinch.

Utilizing the procedure described above, the present invention or PIVOASS secures the intravenous catheter and its tubing in two locations, assists in organizing this tubing and serves to enhance the safe use of the catheter by helping to prevent the dangerous mixing of apinch medications with mainline fluids.

Finally, it should be noted that the foregoing is considered as illustrative only of the principles of the present invention.

Figure 6A:
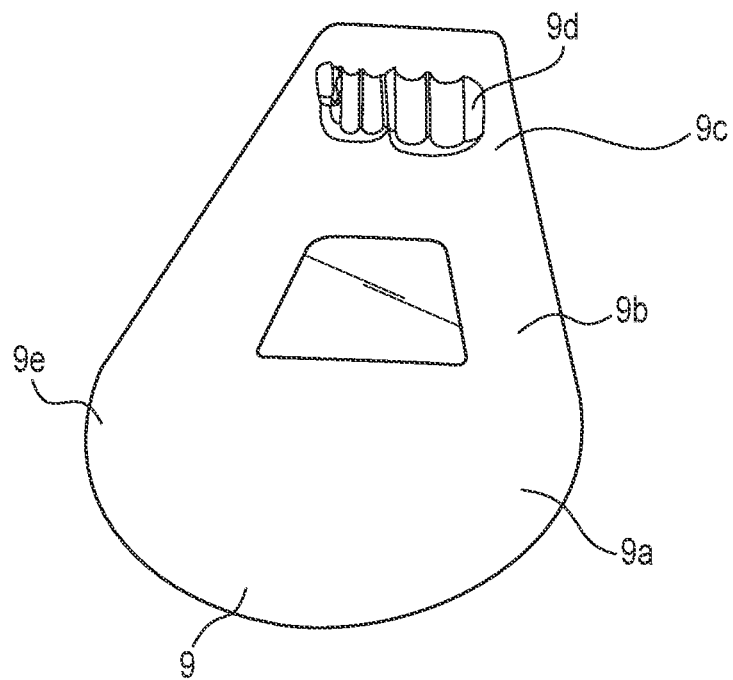
FIG. 6A illustrates the top surface of another version of the preferred embodiment that utilizes a single dressing base which is very similar to the previously described catheter base except that has a longer length with three portions that accommodate an organizer base being mounted in the third portion of its top surface.
Figure 6B:
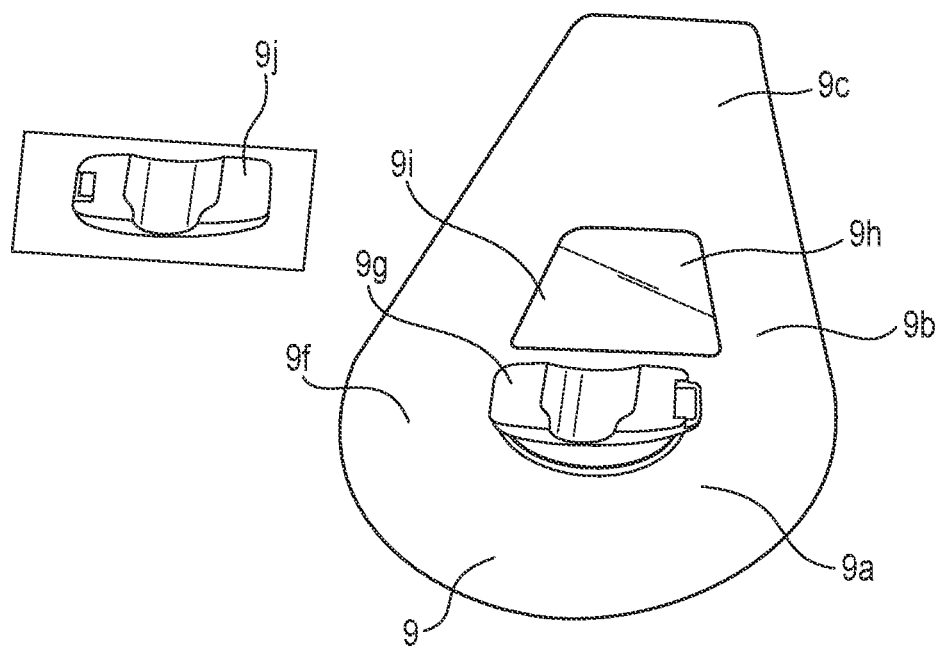
FIG. 6B illustrates the bottom surface of the version whose top surface is shown in FIG. 6A and the still required lower securement element.

For example, another version of this preferred embodiment consists of a dressing base 9 which is very similar to the previously described catheter base except that it has a longer length with three portions 9a-9c that accommodate an organizer base 9d being mounted in the third portion 9c of its top surface 9e. The bottom surface 9f of its first portion 9a contains an upper securement element 9g and its second portion 9b contains an opening 9h with its transparent membrane 9i. Note also the still required lower securement element 9j. See FIGS. 6A-6B.

Since numerous modifications and changes will readily occur to those skilled in the art, it is not desired to limit the invention to the exact construction and operation shown and described herein. Accordingly, all suitable modifications and equivalents may be resorted to, falling within the scope of the invention set forth in the claims in the following section.

I claim:

1. An organizing, safety and securement device for use with a peripheral intravenous catheter, said catheter connecting to a luer fitting, said luer fitting having tubing extending from a distal end thereof, said device comprising:

a catheter base having a boundary edge, a top and a bottom surface; and first and second portions, wherein said first portion includes an opening, that extends between said top surface and said bottom surface, and has a perimeter which at no point coincides with said boundary edge of said catheter base, wherein said opening is totally covered by a transparent membrane, wherein said second portion includes an upper securement element that is attached to said bottom surface of said catheter base, wherein said upper securement element has an upper-securement-element free surface that includes a top luer fitting indentation configured to temporarily enclose a top portion of an outer surface of said luer fitting, a cradle base having a top surface and a bottom surface, a lower securement element, affixed to said top surface of said cradle base, having a top surface that includes a lower-securement-element free surface with a bottom luer fitting indentation configured to temporarily enclose a bottom portion of the outer surface of said luer fitting, an adhesive applied to said bottom surface of said cradle base, an organizer base having a top and a bottom surface, a lower clamping member attached to the top surface of said organizer base, wherein said lower clamping member has a free surface that includes a bottom-portion-tubing indentation configured to temporarily enclose a bottom portion of an outer surface of said tubing, an upper clamping member having a free surface that includes a top-portion-tubing indentation configured to temporarily enclose a top portion of the outer surface of said tubing, a first hinge that connects said upper and lower clamping members and allows them to be rotated about said first hinge between an open position and a closed position, and a tether adapted to connect said catheter base and said organizer base.

2. The organizing, safety and securement device as recited in claim 1, wherein:

said bottom-portion-tubing indentation has both a mainline portion and an apinch portion, and with said mainline portion configured to temporarily enclose a bottom portion of an outer surface of a mainline tubing, and with said apinch portion configured to temporarily enclose a bottom portion of an outer surface of an apinch tubing, and said top-portion-tubing indentation has both a mainline portion and an apinch portion, and with said mainline portion of the top-portion-tubing indentation configured to temporarily enclose a top portion of the outer surface of the mainline tubing, and with said apinch portion of the top-portion-tubing indentation configured to temporarily enclose a top portion of the outer surface of the apinch tubing.

3. The organizing, safety and securement device as recited in claim 2, wherein:

said mainline portion of said bottom-portion-tubing indentation has a color coding that is adapted to remind a device user that only mainline tubing is to be used in said mainline portion of said bottom-portion-tubing indentation, and said apinch portion of said bottom-portion-tubing indentation has a color coding that is adapted to remind the device user that only apinch tubing is to be used in said apinch portion of said bottom-portion-tubing indentation.

4. The organizing, safety and securement device as recited in claim 3, wherein:

said mainline portion of the bottom-portion-tubing indentation and said apinch portion of the bottom-portion-tubing indentation are separate, and wherein said mainline portion of the top-portion-tubing indentation and said apinch portion of the top-portion-tubing indentation are separate, and wherein said mainline portion of the bottom-portion-tubing indentation and said mainline portion of the top-portion-tubing indentation have a second hinge and said apinch portion of the bottom-portion-tubing indentation and said apinch portion of the top-portion-tubing indentation have a third hinge such that said mainline portion of the bottom-portion-tubing indentation and said mainline portion of the top-portion-tubing indentation are enabled to be moved between said open and closed positions independently of said apinch portion of the bottom-portion-tubing indentation and said apinch portion of the top-portion-tubing indentation and said apinch portion of the bottom-portion-tubing indentation and said apinch portion of the top-portion-tubing indentation are enabled to be moved between said open and closed positions independently of said mainline portion of the bottom-portion-tubing indentation and said mainline portion of the top-portion-tubing indentation.

5. The organizing, safety and securement device as recited in claim 2, wherein:

said mainline portion of the bottom-portion-tubing indentation and said apinch portion of the bottom-portion-tubing indentation are separate, and wherein said mainline portion of the top-portion-tubing indentation and said apinch portion of the top-portion-tubing indentation are separate, and wherein said mainline portion of the bottom-portion-tubing indentation and said mainline portion of the top-portion-tubing indentation have a second hinge and said apinch portion of the bottom-portion-tubing indentation and said apinch portion of the top-portion-tubing indentation have a third hinge such that said mainline portion of the bottom-portion-tubing indentation and said mainline portion of the top-portion-tubing indentation are enabled to be moved between said open and closed positions independently of said apinch portion of the bottom-portion-tubing indentation and said apinch portion of the top-portion-tubing indentation and said apinch portion of the bottom-portion-tubing indentation and said apinch portion of the top-portion-tubing indentation are enabled to be moved between said open and closed positions independently of said mainline portion of the bottom-portion-tubing indentation and said mainline portion of the top-portion-tubing indentation.

6. A method of safely and securely attaching a peripheral intravenous catheter, said catheter connecting to a luer fitting, said luer fitting having tubing extending from the distal end of said luer fitting, said method comprising the steps of:

providing a catheter base having a boundary edge, a top and a bottom surface and first and second portions, wherein said first portion includes an opening that extends between said top surface and said bottom surface, and has a perimeter which at no point coincides with said boundary edge of said catheter base, wherein said opening is totally covered by a transparent membrane, wherein said second portion includes an upper securement element that is attached to said bottom surface of said catheter base, wherein said upper securement element has an upper-securement-element free surface that includes a top luer fitting indentation configured to temporarily enclose a top portion of an outer surface of said luer fitting, providing a cradle base having a top surface and a bottom surface, providing a lower securement element, affixed to said top surface of said cradle base, having a top surface that includes a lower-securement-element free surface with a bottom luer fitting indentation configured to temporarily enclose a bottom portion of the outer surface of said luer fitting, applying an adhesive to said bottom surface of said cradle base, providing an organizer base having a top and a bottom surface, attaching a lower clamping member to the top surface of said organizer base, wherein said lower clamping member has a free surface that includes a bottom-portion-tubing indentation configured to temporarily enclose a bottom portion of an outer surface of said tubing, providing an upper clamping member having a free surface that includes a top-portion-tubing indentation configured to temporarily enclose a top portion of the outer surface of said tubing, and providing a first hinge that connects said upper and lower clamping members and allows them to be rotated about said first hinge between an open position and a closed position.

7. The method as recited in claim 6, wherein:

said bottom-portion-tubing indentation has both a mainline portion and an apinch portion, and with said mainline portion configured to temporarily enclose a bottom portion of an outer surface of a mainline tubing, and with said apinch portion configured to temporarily enclose a bottom portion of an outer surface of an apinch tubing, and said top-portion-tubing indentation having both a mainline portion and an apinch portion, and with said mainline portion configured to temporarily enclose a top portion of the outer surface of a mainline tubing, and with said mainline portion of the top-portion-tubing indentation configured to temporarily enclose a top portion of the outer surface of the mainline tubing, and with said apinch portion of the top-portion-tubing indentation configured to temporarily enclose a top portion of the outer surface of an the apinch tubing.

8. The method as recited in claim 7, wherein:

said mainline portion of said bottom-portion-tubing indentation has a color coding that is adapted to remind a device user that only mainline tubing is to be used in said mainline portion of said bottom-portion-tubing indentation, and said apinch portion of said bottom-portion-tubing indentation has a color coding that is adapted to remind the device user that only apinch tubing is to be used in said apinch portion of said bottom-portion-tubing indentation.

9. The method as recited in claim 7, wherein:

said mainline portion of the bottom-portion-tubing indentation and said apinch portion of the bottom-portion-tubing indentation are separate, and wherein said mainline portion of the top-portion-tubing indentation and said apinch portion of the top-portion-tubing indentation are separate, and wherein said mainline portion of the bottom-portion-tubing indentation and said mainline portion of the top-portion-tubing indentation have a second hinge and said apinch portion of the bottom-portion-tubing indentation and said apinch portion of the top-portion-tubing indentation have a third hinge such that said mainline portion of the bottom-portion-tubing indentation and said mainline portion of the top-portion-tubing indentation are enabled to be moved between said open and closed positions independently of said apinch portion of the bottom-portion-tubing indentation and said apinch portion of the top-portion-tubing indentation and said apinch portion of the bottom-portion-tubing indentation and said apinch portion of the top-portion-tubing indentation are enabled to be moved between said open and closed positions independently of said mainline portion of the bottom-portion-tubing indentation and said mainline portion of the top-portion-tubing indentation.

10. The method as recited in claim 7, wherein:

said mainline portion of the bottom-portion-tubing indentation and said apinch portion of the bottom-portion-tubing indentation are separate, and wherein said mainline portion of the top-portion-tubing indentation and said apinch portion of the top-portion-tubing indentation are separate, and wherein said mainline portion of the bottom-portion-tubing indentation and said mainline portion of the top-portion-tubing indentation have a second hinge and said apinch portion of the bottom-portion-tubing indentation and said apinch portion of the top-portion-tubing indentation have a third hinge such that said mainline portion of the bottom-portion-tubing indentation and said mainline portion of the top-portion-tubing indentation are enabled to be moved between said open and closed positions independently of said apinch portion of the bottom-portion-tubing indentation and said apinch portion of the top-portion-tubing indentation and said apinch portion of the bottom-portion-tubing indentation and said apinch portion of the top-portion-tubing indentation are enabled to be moved between said open and closed positions independently of said mainline portion of the bottom-portion-tubing indentation and said mainline portion of the top-portion-tubing indentation.

\* \* \* \* \*